US012728176B2

(12) United States Patent
Ludwig

(10) Patent No.: US 12,728,176 B2
(45) Date of Patent: Sep. 8, 2026

(54) COMPOSITIONS AND METHODS OF IMMUNODEPLETION FOR THE TREATMENT OF MALIGNANT AND NON-MALIGNANT HEMATOLOGICAL DISEASES

(71) Applicant: ACTINIUM PHARMACEUTICALS, INC., New York, NY (US)

(72) Inventor: Dale L. Ludwig, Rockaway, NJ (US)

(73) Assignee: ACTINIUM PHARMACEUTICALS, INC., New York, NY (US)

( * ) Notice: Subject to any disclaimer, the term of this patent is extended or adjusted under 35 U.S.C. 154(b) by 1229 days.

(21) Appl. No.: 17/606,254

(22) PCT Filed: Apr. 24, 2020

(86) PCT No.: PCT/US2020/029790

§ 371 (c)(1),
(2) Date: Oct. 25, 2021

(87) PCT Pub. No.: WO2020/219861

PCT Pub. Date: Oct. 29, 2020

(65) Prior Publication Data

US 2022/0211885 A1 Jul. 7, 2022

Related U.S. Application Data

(60) Provisional application No. 62/838,589, filed on Apr. 25, 2019.

(51) Int. Cl.

| | |
|---|---|
| ***A61K 51/10*** | (2006.01) |
| ***A61K 35/28*** | (2015.01) |
| ***A61K 39/00*** | (2006.01) |
| ***A61P 35/02*** | (2006.01) |
| ***C07K 16/28*** | (2006.01) |

(52) U.S. Cl.

CPC .......... *A61K 51/1027* (2013.01); *A61K 35/28* (2013.01); *A61K 51/103* (2013.01); *A61P 35/02* (2018.01); *C07K 16/2803* (2013.01); *C07K 16/2863* (2013.01); *C07K 16/2896* (2013.01); *A61K 2039/505* (2013.01); *A61K 2039/545* (2013.01)

(58) Field of Classification Search

CPC .... A61K 51/00; A61K 51/1027; A61K 35/00; A61K 35/28; A61K 51/103; A61K 2039/505; A61K 2039/545; A61K 51/1093; A61K 39/3955; A61P 35/02; C07K 16/2803; C07K 16/2863; C07K 16/2896

See application file for complete search history.

(56) References Cited

U.S. PATENT DOCUMENTS

| | | | | |
|---|---|---|---|---|
| 5,489,516 | A | 2/1996 | Broudy et al. | |
| 5,548,065 | A | 8/1996 | Lemischka | |
| 5,595,721 | A | 1/1997 | Kaminski et al. | |
| 5,635,388 | A | 6/1997 | Bennett | |
| 5,843,633 | A | 12/1998 | Yin et al. | |
| 7,183,385 | B2 | 2/2007 | Comb et al. | |
| 7,850,960 | B2 * | 12/2010 | Moon | G01N 33/5041 435/372 |
| 2012/0134979 | A1 | 5/2012 | Xia et al. | |
| 2014/0234298 | A1 | 8/2014 | Steidl | |
| 2017/0224737 | A1 | 8/2017 | Shizuru et al. | |
| 2018/0187173 | A1 | 7/2018 | Cost et al. | |

FOREIGN PATENT DOCUMENTS

| | | |
|---|---|---|
| WO | WO 00/09160 | 2/2000 |
| WO | WO 02/080987 | 10/2002 |
| WO | WO 2004/002425 | 1/2004 |
| WO | 2013175237 A1 | 11/2013 |
| WO | 2016187514 A1 | 11/2016 |
| WO | 2017155937 A1 | 9/2017 |
| WO | 2017205587 A1 | 11/2017 |
| WO | WO 2017/219025 | 12/2017 |
| WO | WO 2018/183613 | 10/2018 |
| WO | WO 2019/027973 | 2/2019 |
| WO | WO 2019/084248 | 5/2019 |
| WO | WO 2019/084258 | 5/2019 |

OTHER PUBLICATIONS

Buckley et al, American Society of Hematology, pp. 584-595 (Year: 2015).*

Navarro et al, Bioconjugate Chem., Aug. 2019, vol. 30, pp. 2393-2403 (Year: 2019).*

Czechowicz et al., Selective hematopoietic stem cell ablation using CD117-antibody-drug-conjugates enables safe and effective transplantation with immunity preservation.

Ludwig et al., “Lymphodepletion with CD45 Radioimmunotherapy as a Targeted Conditioning Regimen Prior to Adoptive Cell Therapy or CAR-T”.

Extended European Search Report dated Apr. 11, 2023 for corresponding European Patent Application No. 20796153.3.

Extended European Search Report dated Apr. 11, 2023 for corresponding European Patent Application No. 20794715.1

International Search Report and Written Opinion dated Oct. 5, 2020 for corresponding International Application No. PCT/US2020/029887.

(Continued)

*Primary Examiner* — D. L. Jones

(74) *Attorney, Agent, or Firm* — Dentons Cohen & Grigsby, P.C.; Michael E. Dukes

(57) ABSTRACT

This invention provides a method for depleting a subject's hematopoietic stem cells that includes administering to the subject an effective amount of a radiolabeled antibody against CD34, CD117, or CD135, where preferred radiolabels include $^{131}$I and $^{225}$Ac. This invention also provides a method for treating a subject afflicted with a non-cancerous disorder treatable via genetically edited cell therapy, where the method includes (i) administering to the subject an amount of the radiolabeled antibody effective to deplete the subject's hematopoietic stem cells, and (ii) after a suitable time period, performing the therapy on the subject to treat the subject's disorder. Finally, this invention provides articles of manufacture for performing the subject methods.

18 Claims, No Drawings

(56) References Cited

OTHER PUBLICATIONS

International Search Report and Written Opinion dated Sep. 18, 2020 for corresponding International Application No. PCT/US2020/029790.
Dever et al., "CRISPR/Cas9 Beta-globin Gene Targeting in Human Hematopoietic Stem Cells", Nature. Nov. 17, 2016; 539(7629): 384-389.
Alzubi et al., "Targeted genome editing restores T cell differentiation in a humanized X-SCID pluripotent stem cell disease model", Scientific Reports 2017; 7: 12475, 1-11.
Chang et al., "Modeling Human Severe Combined Immunodeficiency and Correction by CRISPR/Cas9-Enhanced Gene Targeting", Cell Reports 2015, 12, 1668-1677.
Yao et al., "Levels of peripheral CD4+FoxP3+ regulatory T cells are negatively associated with clinical response to adoptive immunotherapy of human cancer", Blood, Jun. 2012, 119(24):5688-5696.
Newick et al., "Chimeric antigen receptor T-cell therapy for solid tumors", Molecular Therapy—Oncolytics (2016) 3, 16006, 7 pgs.
D'Aloia et al., "CAR-T cells: the long and winding road to solid tumors", Cell Death and Disease (2018) 9:282, 12 pgs.
Ren et al., "Multiplex Genome Editing to Generate Universal Car T Cells Resistant to PD1 Inhibition", Clin Cancer Res 2017; 23(9):2255-2266.
Giavridis et al., "CAR T cell-induced cytokine release syndrome is mediated by macrophages and abated by IL-1 blockade", Nat Med. Jun. 2018; 24(6): 731-738.
Eyquem et al., "Targeting a CAR to the TRAC locus with CRISPR/Cas9 enhances tumour rejection", Nature. Mar. 2, 2017; 543(7643): 113-117, 28 pgs.
Gattinoni et al., "Removal of homeostatic cytokine sinks by lymphodepletion enhances the efficacy of adoptively transferred tumor-specific CD8+ T cells", JEM vol. 202, No. 7, Oct. 3, 2005 907-912.
Sun et al., "Seamless correction of the sickle cell disease mutation of the HBB gene in human induced pluripotent stem cells using TALENs," Biotechnol. Biotechnol. Bioeng. 2014; 111(5): 1048-1053.
Hagenbeek et al., "Radioimmunotherapy for NHL: Experience of 90Y-Ibritumomab Tiuxetan in Clinical Practice", Leukemia & Lymphoma, 2003 vol. 44 Supplement 4, pp. S37-S47.
Onea et al., "CD19 chimeric antigen receptor (CD19 CAR)-redirected adoptive T-cell immunotherapy for the treatment of relapsed or refractory B-cell Non-Hodgkin's Lymphomas", Am J Cancer Res 2016; 6(2):403-424.
Atsuo, T., Usage of conventional immunosuppressive drugs (cyclophosphamide and azathioprine), Japanese Journal of Internal Medicine, 2009, vol. 98, No. 10, p. 2500-2505, <DOI: 10.2169/naika.98.2500>.

* cited by examiner

COMPOSITIONS AND METHODS OF IMMUNODEPLETION FOR THE TREATMENT OF MALIGNANT AND NON-MALIGNANT HEMATOLOGICAL DISEASES

CROSS-REFERENCE TO RELATED APPLICATIONS

This is a national stage application filed under 35 U.S.C. 371 based on International Patent Application No. PCT/US2020/029790, filed Apr. 24, 2020, which claims priority to U.S. Provisional Patent Application Ser. No. 62/838,589 filed on Apr. 25, 2019, the disclosures of which are incorporated herein by reference in their entireties.

FIELD OF THE INVENTION

The present invention relates to compositions useful for selective depletion and ablation of hematopoietic stem cells and uses thereof in methods of treatment of malignant and non-malignant hematological diseases.

BACKGROUND OF THE INVENTION

Hematopoietic stem cell transplant (HSCT) is primarily indicated to treat malignancies and requires conditioning of the subject's tissues (e.g., bone marrow tissue) prior to engraftment. HSCT indications and hemoglobinopathies include, for example, sickle cell anemia, beta thalassemia, Wiskott-Aldrich syndrome, adenosine deaminase severe combined immunodeficiency disease (ADA SCID), metachromatic leukodystrophy and HIV/AIDS; the list of indications will continue to expand with improvement in gene editing technologies. In certain instances, 20% engraftment of transplanted cells may alleviate or cure the disease.

Gene editing technologies have advanced substantially with the advent of site-specific editing methods, such as TALEN, CRISPR/cas9, and zinc finger nuclease (ZFN) methods. These methods have therapeutic potential for patients afflicted with non-malignant hereditary diseases such as hemoglobinopathies, congenital immunodeficiencies, and viral-based disorders like AIDS. Gene editing technology makes it feasible to treat and even cure, for example, germline blood disorders such as severe combined immunodeficiency disease (SCID), sickle cell disease (SCD), and β-thalassemia.

Gene editing precisely and permanently alters a sequence of genomic DNA that remains under endogenous genetic regulation and control for proper and appropriate expression of the modified genetic element. There are presently four major classes of nucleases for human genome gene editing: zinc finger nucleases (ZFNs), transcription activator-like effector nucleases (TALENs), meganucleases (MNs), and clustered regularly interspaced short palindromic repeats (CRISPR/Cas9). Each of these can recognize and bind a specific target sequence of DNA. Depending on the properties of the approach, the target DNA can be cleaved on one or both strands. To correct a mutation, a correction template is used for homology-directed repair of the introduced break at the site of the targeted lesion.

Current non-targeted conditioning methods, which include, for example, irradiation (e.g., total body irradiation or TBI) and DNA alkylating/modifying agents, are highly toxic to multiple organ systems, hematopoietic and non-hematopoietic cells and the hematopoietic microenvironment. These harsh conditioning regimens effectively kill the host subject's immune and niche cells and adversely affect multiple organ systems, frequently leading to life-threatening complications.

To fully realize the curative potential of HSCT, the development of mild-conditioning regimens that avoid undesirable toxicity is essential. Needed are novel, preferably non-myeloablative, compositions and methods that may be used to condition a subject's tissues (e.g., bone marrow tissues), while lessening undesirable toxicity and minimizing the incidence of serious adverse reactions. Also needed are novel therapies that can selectively ablate an endogenous hematopoietic stem cell population in a target tissue, while minimizing or eliminating the effects of such therapies on non-targeted cells and tissues, such as platelets, white blood cells and red blood cells. Also needed are assays and methods for identifying agents that can selectively deplete or ablate an endogenous hematopoietic stem cell population.

SUMMARY OF THE INVENTION

This invention provides methods and compositions useful for targeted depletion of a subject's hematopoietic stem cells comprising administering to the subject an effective amount of a radiolabeled antibody, wherein the antibody is selected from one or more of anti-CD34, anti-CD117, or anti-CD135. The antibodies may comprise a radiolabel selected from $^{131}$I, $^{125}$I, $^{123}$I, $^{90}$Y, $^{177}$Lu, $^{186}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb and $^{103}$Pd.

This invention also provides methods for targeted depletion of a subject's hematopoietic stem cells to condition the subject's tissue for engraftment or transplant. As such, the invention provides a method for treating a subject afflicted with a cancerous disorder treatable with a bone marrow transplant comprising (i) administering to the subject an amount of the radiolabeled antibody effective to substantially deplete or ablate the subject's hematopoietic stem cells, and optionally, (ii) after a suitable time period, performing the bone marrow transplant on the subject.

The invention further provides methods for treating a subject afflicted with a non-cancerous disorder treatable via genetically edited cell therapy comprising (i) administering to the subject an amount of the radiolabeled antibody effective to deplete the subject's hematopoietic stem cells, and optionally, (ii) after a suitable time period, performing the therapy on the subject to treat the subject's disorder.

Finally, this invention provides an article of manufacture comprising (a) at least one of the radiolabeled antibodies described hereinabove, and (b) a label instructing the user to administer to a subject an amount of the antibody effective to deplete the subject's hematopoietic stem cells.

According to certain aspects, the radiolabel on the antibody, i.e., anti-CD34, anti-CD117, or anti-CD135, may be $^{131}$I or $^{225}$Ac, wherein an effective amount of an $^{131}$I-labeled antibody may be up to 1200 mCi (e.g., 10 to 200 mCi, 200 to 400 mCi, or 400 to 1,200 mCi), and an effective amount of an $^{225}$Ac-labeled antibody may be up to 5.0 μCi/kg of subject weight (e.g., 0.1 μCi/kg to 5.0 μCi/kg, 0.1 μCi/kg to 1.0 μCi/kg subject weight, 1.0 μCi/kg to 3.0 μCi/kg subject weight, 3.0 μCi/kg to 5.0 μCi/kg subject weight).

DETAILED DESCRIPTION OF THE INVENTION

This invention provides radiolabeled antibody-based methods for depleting a subject's hematopoietic stem cells, and related methods and articles of manufacture. When these methods precede certain gene-edited cell-based therapies, the methods are able to enhance the outcome of those therapies while minimizing adverse effects.

Throughout this application, various publications are cited. The disclosure of these publications is hereby incorporated by reference into this application to describe more fully the state of the art to which this invention pertains.

Definitions

In this application, certain terms are used which shall have the meanings set forth as follows.

The singular forms "a," "an," "the" and the like include plural referents unless the context clearly dictates otherwise. Thus, for example, reference to "an" antibody includes both a single antibody and a plurality of different antibodies.

The term "about" when used before a numerical designation, e.g., temperature, time, amount, and concentration, including a range, indicates approximations which may vary by ±10%, ±5%, or ±1%.

As used herein, "administer", with respect to an antibody, means to deliver the antibody to a subject's body via any known method suitable for antibody delivery. Specific modes of administration include, without limitation, intravenous, transdermal, subcutaneous, intraperitoneal and intrathecal administration. Exemplary administration methods for antibodies may be as substantially described in International Publication No. WO 2016/187514, incorporated by reference herein.

In addition, in this invention, antibodies can be formulated using one or more routinely used pharmaceutically acceptable carriers. Such carriers are well known to those skilled in the art. For example, injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's).

As used herein, the term "antibody" includes, without limitation, (a) an immunoglobulin molecule comprising two heavy chains and two light chains and which recognizes an antigen; (b) polyclonal and monoclonal immunoglobulin molecules; (c) monovalent and divalent fragments thereof (e.g., Fab, di-Fab), and (d) bi-specific forms thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring (e.g., IgG-Fc-silent). Furthermore, antibodies include chimeric antibodies, wholly synthetic antibodies, single chain antibodies (e.g., scFv), single and double domain antibodies (e.g., VHH), and fragments thereof. Antibodies may be human, humanized or nonhuman.

"Monoclonal antibody" refers to a preparation of antibody molecules of single molecular composition. A monoclonal antibody composition displays a single binding specificity and affinity for a particular epitope, or in a case of a multi-specific monoclonal antibody, a binding specificity to two or more distinct epitopes. "Monoclonal antibody" therefore refers to an antibody population with single amino acid composition in each heavy and each light chain, except for possible well-known alterations such as removal of C-terminal lysine from the antibody heavy chain. Monoclonal antibodies may have heterogeneous glycosylation within the antibody population. Monoclonal antibodies may be monospecific or multi-specific, or monovalent, bivalent or multivalent.

As used herein, an "anti-CDXX antibody" is an antibody that binds to any available epitope of CDXX, wherein the XX may be 34, 117, or 135 (i.e., CD34, CD117, or CD135). An anti-CDXX antibody may be a bispecific antibody that binds to two different epitopes, wherein the epitopes may include any one of the CD34, CD117, or CD135, and another relevant epitope (e.g., CD45); or may be two different epitopes of a single cell surface target (two different epitopes of any one of CD34, CD117, or CD135). The bispecific antibody may be a recombinant antibody, a monoclonal antibody, a chimeric antibody, a humanized antibody, a human antibody, or an antibody fragment.

As used herein, "depleting", with respect to a subject's hematopoietic stem cells ("HSCs", i.e., multipotential hematopoietic stem cells, also referred to as hemocytoblasts) shall mean to lower the population of the subject's HSCs. According to certain aspects, depleting a subject's HSCs means reducing the subject's HSC population by at least 10%, 20%, 30%, 40%, 50%, 60%, 70%, 80%, 90%, 95% or 99%. According to certain aspects, depleting a subject's HSCs means reducing the subject's HSC population by 100%. Methods for measuring HSC populations are routine. They include, for example, the use of flow cytometry to detect human HSCs in a bone marrow sample and staining for various cell surface markers (such as Lin, CD34, CD38, CD43, CD45RO, CD45RA, CD59, CD90, CD109, CD117, CD133, CD166, and HLA DR). Reduction of a patient's immune cells may also be detected in peripheral blood. This can be accomplished, for example, by determining absolute lymphocyte counts (ALCs) via detection of CD3-, CD4- and CD8-positive cells as an indication of immune suppression.

As used herein, the term "targeted depletion," with respect to a subject's hematopoietic stem cells (HSC) shall mean to substantially lower the population of the subject's HSCs, as indicated above, while substantially leaving the population of mature differentiated hematopoietic stem cells unaffected. For example, targeted depletion may be taken to mean that the non-targeted mature differentiated hematopoietic stem cells (e.g., lymphoid, myeloid, etc.) are depleted by less than 20%, or less than 10%.

As used herein, an amount of a radiolabeled antibody, when administered, is "effective" if it reduces the subject's HSC level.

According to aspects where the radiolabeled antibody is labeled with $^{131}I$, the effective amount is below, for example, 1,200 mCi (i.e., where the amount of $^{131}I$ administered to the subject delivers a total body radiation dose of below 1,200 mCi).

According to aspects where the radiolabeled antibody is labeled with $^{131}I$, the effective amount is below 1,100 mCi, below 1,000 mCi, below 900 mCi, below 800 mCi, below 700 mCi, below 600 mCi, below 500 mCi, below 400 mCi, below 350 mCi, below 300 mCi, below 250 mCi, below 200 mCi, below 150 mCi, below 100 mCi, below 50 mCi, below 40 mCi, below 30 mCi, below 20 mCi or below 10 mCi.

According to aspects where radiolabeled antibody is labeled with $^{131}I$, the effective amount is from 1 mCi to 10 mCi, from 1 mCi to 200 mCi, from 10 mCi to 20 mCi, from 10 mCi to 30 mCi, from 10 mCi to 40 mCi, from 10 mCi to 50 mCi, from 10 mCi to 100 mCi, from 10 mCi to 150 mCi, from 10 mCi to 200 mCi, from 20 mCi to 30 mCi, from 30 mCi to 40 mCi, from 40 mCi to 50 mCi, from 50 mCi to 100 mCi, from 50 mCi to 150 mCi, from 50 mCi to 200 mCi, from 60 mCi to 140 mCi, from 70 mCi to 130 mCi, from 80 mCi to 120 mCi, from 90 mCi to 110 mCi, from 100 mCi to 150 mCi, from 150 mCi to 200 mCi, from 200 mCi to 250 mCi, from 200 mCi to 300 mCi, from 200 mCi to 350 mCi, from 200 mCi to 400 mCi, from 200 mCi to 500 mCi, from 200 mCi to 600 mCi, from 200 mCi to 700 mCi, from 200 mCi to 800 mCi, from 200 mCi to 900 mCi, from 200 mCi to 1,000 mCi, from 200 mCi to 1,100 mCi, from 200 mCi to 1,200 mCi, from 400 mCi to 500 mCi, from 400 mCi to 600 mCi, from 400 mCi to 700 mCi, from 400 mCi to 800 mCi, from 400 mCi to 900 mCi, from 400 mCi to 1,000 mCi, from 400 mCi to 1,100 mCi, or from 400 mCi to 1,200 mCi.

According to aspects where radiolabeled antibody is labeled with $^{131}$I, the effective amount is 1 mCi, 10 mCi, 20 mCi, 30 mCi, 40 mCi, 50 mCi, 60 mCi, 70 mCi, 80 mCi, 90 mCi, 100 mCi, 110 mCi, 120 mCi, 130 mCi, 140 mCi, 150 mCi, 200 mCi, 250 mCi, 300 mCi, 350 mCi, 400 mCi, 450 mCi, 500 mCi, 550 mCi, 600 mCi, 650 mCi, 700 mCi, 750 mCi, 800 mCi, 850 mCi, 900 mCi, 950 mCi, 1,000 mCi, 1,050 mCi, 1,100 mCi, 1,150 mCi, or 1,200 mCi.

According to aspects where the radiolabeled antibody is labeled with $^{225}$Ac, the effective amount is below, for example, 5.0 μCi/kg (i.e., where the amount of $^{225}$Ac-anti-CDXX administered to the subject delivers a radiation dose of below 5.0 μCi per kilogram of subject's body weight).

According to aspects where the radiolabeled antibody is labeled with $^{225}$Ac, the effective amount is below 4.5 μCi/kg, 4.0 μCi/kg, 3.5 μCi/kg, 3.0 μCi/kg, 2.5 μCi/kg, 2.0 μCi/kg, 1.5 μCi/kg, 1.0 μCi/kg, 0.9 μCi/kg, 0.8 μCi/kg, 0.7 μCi/kg, 0.6 μCi/kg, 0.5 μCi/kg, 0.4 μCi/kg, 0.3 μCi/kg, 0.2 μCi/kg, 0.1 μCi/kg or 0.05 μCi/kg.

According to aspects where the radiolabeled antibody is labeled with $^{225}$Ac, the effective amount is from 0.05 μCi/kg to 0.1 μCi/kg, from 0.1 μCi/kg to 0.2 μCi/kg, from 0.2 μCi/kg to 0.3 μCi/kg, from 0.3 μCi/kg to 0.4 μCi/kg, from 0.4 μCi/kg to 0.5 μCi/kg, from 0.5 μCi/kg to 0.6 μCi/kg, from 0.6 μCi/kg to 0.7 μCi/kg, from 0.7 μCi/kg to 0.8 μCi/kg, from 0.8 μCi/kg to 0.9 μCi/kg, from 0.9 μCi/kg to 1.0 μCi/kg, from 1.0 μCi/kg to 1.5 μCi/kg, from 1.5 μCi/kg to 2.0 μCi/kg, from 2.0 μCi/kg to 2.5 μCi/kg, from 2.5 μCi/kg to 3.0 μCi/kg, from 3.0 μCi/kg to 3.5 μCi/kg, from 3.5 μCi/kg to 4.0 μCi/kg, from 4.0 μCi/kg to 4.5 μCi/kg, or from 4.5 μCi/kg to 5.0 μCi/kg.

According to aspects where the radiolabeled antibody is labeled with $^{225}$Ac, the effective amount is 0.05 μCi/kg, 0.1 μCi/kg, 0.2 μCi/kg, 0.3 μCi/kg, 0.4 μCi/kg, 0.5 μCi/kg, 0.6 μCi/kg, 0.7 μCi/kg, 0.8 μCi/kg, 0.9 μCi/kg, 1.0 μCi/kg, 1.5 μCi/kg, 2.0 μCi/kg, 2.5 μCi/kg, 3.0 μCi/kg, 3.5 μCi/kg, 4.0 μCi/kg or 4.5 μCi/kg.

The effective amount of the radiolabeled antibody may be provided as a single dose. A majority of the antibody administered to a subject typically consists of non-labeled antibody, with the minority being the labeled antibody. The ratio of labeled to non-labeled antibody can be adjusted using known methods. Thus, accordingly to certain aspects of the present invention, the antibody may be provided in a total protein amount of up to 100 mg, such as less than 60 mg, or from 5 mg to 45 mg, or a total protein amount of between 0.1 μg/kg to 1 mg/kg patient weight, such as 1 ug/kg to 1 mg/kg patient weight, or 10 ug/kg to 1 mg/kg patient weight, or 100 ug/kg to 1 mg/kg patient weight, or 0.1 ug/kg to 100 ug/kg patient weight, or 0.1 ug/kg to 50 ug/kg patient weight, or 0.1 ug/kg to 10 ug/kg patient weight, or 0.1 ug/kg to 40 ug/kg patient weight, or 1 ug/kg to 40 ug/kg patient weight, or 0.1 mg/kg to 1.0 mg/kg patient weight, such as from 0.2 mg/kg patient weight to 0.6 mg/kg patient weight.

According to certain aspects of the present invention, the radiolabeled antibody may comprise a labeled fraction and an unlabeled fraction, wherein the ratio of labeled:unlabeled may be from about 0.01:10 to 1:1, such as 0.1:10 to 1:1 labeled:unlabeled.

Moreover, the radiolabeled antibody may be provided as a single dose composition tailored to a specific patient, i.e., as a patient specific therapeutic composition, wherein the amount of labeled and unlabeled antibody in the composition may depend on at least a patient weight, height, body surface area, age, gender, and/or disease state or health status. As such, a total volume of the patient specific therapeutic composition may be provided in a vial that is configured to be wholly administered to the patient in one treatment session, such that little to no composition remains in the vial after administration.

A "hematologic malignancy" or "malignant hematological disease", also known as a blood cancer, is a cancer that originates in blood-forming tissue, such as the bone marrow or other cells of the immune system. Hematologic malignancies include, without limitation, leukemias (such as acute myeloid leukemia (AML), acute promyelocytic leukemia, acute lymphoblastic leukemia (ALL), acute mixed lineage leukemia, chronic myeloid leukemia, chronic lymphocytic leukemia (CLL), hairy cell leukemia and large granular lymphocytic leukemia), myelodysplastic syndrome (MDS), myeloproliferative disorders (polycythemia vera, essential thrombocytosis, primary myelofibrosis and chronic myeloid leukemia), lymphomas, multiple myeloma, MGUS and similar disorders, Hodgkin's lymphoma, non-Hodgkin's lymphoma (NHL), primary mediastinal large B-cell lymphoma, diffuse large B-cell lymphoma, follicular lymphoma, transformed follicular lymphoma, splenic marginal zone lymphoma, lymphocytic lymphoma, T-cell lymphoma, and other B-cell malignancies.

"Solid cancers" include, without limitation, bone cancer, pancreatic cancer, skin cancer, cancer of the head or neck, cutaneous or intraocular malignant melanoma, uterine cancer, ovarian cancer, prostate cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, pediatric tumors, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally-induced cancers including those induced by asbestos.

A "non-malignant hematological disease" or "non-cancerous disorder" includes, without limitation, Type I diabetes; hemoglobinopathies (e.g., SCD and β-thalassemia); congenital immunodeficiencies (e.g., SCID); and viral infections (e.g., HIV infection). According to certain aspects, the disorder is SCD and the therapy is genetically edited β-globin hematopoietic stem cell therapy. The stem cell therapy can be allogeneic or autologous, for example. According to certain aspects, the disorder is SCID and the therapy is genetically edited hematopoietic stem cell therapy, wherein the edited gene is the common gamma chain (γc) gene, the adenosine deaminase (ADA) gene and/or the Janus kinase 3 (JAK3) gene. The stem cell therapy can be allogeneic or autologous, for example.

As used herein, the term "subject" includes, without limitation, a mammal such as a human, a non-human primate, a dog, a cat, a horse, a sheep, a goat, a cow, a rabbit, a pig, a rat and a mouse. Where the subject is human, the subject can be of any age. According to certain aspects, the subject is an infant. According to further aspects, the subject is one, two, three, four, five, six, seven, eight, nine or 10. According to yet further aspects, the subject is from 10 to 15, or from 15 to 20. According to yet further aspects, the subject is 20 or older, 25 or older, 30 or older, 35 or older, 40 or older, 45 or older, 50 or older, 55 or older, 60 or older, 65 or older, 70 or older, 75 or older, 80 or older, 85 or older, or 90 or older.

As used herein, a "suitable time period" after administering a radiolabeled antibody to a subject and before performing therapy on the subject is a time period sufficient to permit the administered antibody to deplete the subject's HSCs and/or for the subject's HSCs to remain depleted. According to certain aspects, the suitable time period is fewer than 15 days, fewer than 14 days, fewer than 13 days, fewer than 12 days, fewer than 11 days, fewer than 10 days, fewer than 9 days, fewer than 8 days, fewer than 7 days, fewer than 6 days, fewer than 5 days, fewer than 4 days, or fewer than 3 days. According to certain aspects, the suitable time period is 1 day, 2 days, 3 days, 4 days, 5 days, 6 days, 7 days, 8 days, 9 days, 10 days, 11 days, 12 days, 13 days, 14 days, 15 days, or more than 15 days.

As used herein, a "radioisotope" can be an alpha-emitting isotope, a beta-emitting isotope, and/or a gamma-emitting isotope. Examples of radioisotopes include the following: $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb and $^{103}$Pd. Methods for affixing a radioisotope to an antibody (i.e., "labeling" an antibody with a radioisotope) are well known. Certain of these methods are described, for example, in International Publication No. WO 2017/155937.

As used herein, "treating" a subject afflicted with a disorder shall include, without limitation, (i) slowing, stopping or reversing the disorder's progression, (ii) slowing, stopping or reversing the progression of the disorder's symptoms, (iii) reducing, and ideally eliminating, the likelihood of the disorder's recurrence, and/or (iv) reducing, and ideally eliminating, the likelihood that the disorder's symptoms will recur. According to certain preferred aspects, treating a subject afflicted with a disorder means (i) reversing the disorder's progression, ideally to the point of eliminating the disorder, and/or (ii) reversing the progression of the disorder's symptoms, ideally to the point of eliminating the symptoms, and/or (iii) reducing or eliminating the likelihood of relapse. Ideally, treating a subject afflicted with a disorder means curing the disorder by removing or otherwise disabling its genetic cause.

Throughout this application, various publications are cited. The disclosure of these publications is hereby incorporated by reference into this application to describe more fully the state of the art to which this invention pertains. Unless otherwise defined, all technical and scientific terms used herein have the same meaning as commonly understood by one of ordinary skill in the art to which the present invention belongs. Although methods and materials similar or equivalent to those described herein can be used in the practice or testing described herein, suitable methods and materials are described below.

Aspects of the Invention

This invention solves an unmet need in the art by providing an unexpectedly superior way to deplete a subject's hematopoietic stem cells, ideally prior to bone marrow transplant or a gene-edited cell-based therapy like genetically edited β-globin hematopoietic stem cell therapy for SCD. This invention employs a radiolabeled antibody for this purpose, such as a radiolabeled anti-CD34, anti-CD117, or anti-CD135. The antibody can safely and effectively deplete the subject's hematopoietic stem cells via targeted conditioning. This approach avoids certain adverse effects caused by less specific agents like chemotherapeutics or external beam radiation.

CD34 is a 105 kD to 120 kD glycosylated type-I transmembrane protein that is specifically expressed on the surfaces of hematopoietic stem/progenitor cells (HSC/HPC) of human beings and other mammals. Two transcript variants encoding different isoforms have been found for the CD34 gene. It functions as a cell-cell adhesion factor and mediates the attachment of stem cells to bone marrow extracellular matrix or directly to stromal cells. Expression of CD34 gradually decreases with maturity of hematopoietic cells. CD34 is also expressed in normal and tumorous microvascular endothelial cells. Anti-CD34 antibodies that can be used in conjunction with the targeted depletion methods described herein include, without limitation, antibodies produced and released from ATCC Accession No. AC133.1 and HB 12346, as described, for example, in U.S. Pat. No. 5,843,633.

CD117, or mast/stem cell growth factor receptor (SCFR), or c-Kit, is a receptor tyrosine kinase protein that in humans is encoded by the KIT gene. Multiple transcript variants encoding different isoforms have been found for this gene. Stem cell factor (SCF) signals through CD117 in a pathway that plays a key role in hematopoiesis. CD117 is expressed on pluripotent hematopoietic stem cells which are the precursors to mature cells belonging to lymphoid and erythroid lineages. While other mature hematopoietic cells show reduced or no expression of CD117, mast cell precursors and mature mast cells retain high levels of CD117 expression. Hence SCF signaling via CD117 is vital for mast cell development, function, trafficking and survival. Exemplary commercially available anti-CD117 antibodies include IMC-CK6, AMG191, KTN0158, A3C6E2 and LMJ729.

Other anti-CD117 antibodies that can be used in conjunction with the targeted depletion methods described herein include, for instance, antibodies produced and released from ATCC Accession No. 10716 (deposited as BA7.3C.9), such as the SR-1 antibody, which is described, for example, in U.S. Pat. No. 5,489,516.

CD135, or Ly72, Flk-2, Flt-3, or B230315G04, is a type I transmembrane cytokine receptor that belongs to the receptor tyrosine kinase class III. CD135 is the receptor for the cytokine Flt3 ligand (FLT3L). Signaling of CD135 is important for the normal development of hematopoietic stem cells and progenitor cells. It is expressed on the surface of many hematopoietic progenitor cells and is found on a majority of malignant hematopoietic cells (e.g., AML, ALL). Although, CD135 expression is usually lost upon hematopoietic stem cell (HSC) differentiation, dendritic cells are an exception, as mature dendritic cells (DCs)

display persistent CD135 expression. Exemplary commercially available anti-CD135 antibodies include LY3012218 (IMC-EB10).

Other anti-CD135 antibodies that can be used in conjunction with the targeted depletion methods described herein include, for instance, antibodies produced and released by American Type Culture Collection (ATCC) Accession No. ATCC HB 11,557, which is described, for example, in U.S. Pat. No. 5,635,388; or antibodies produced and released by ATCC Accession No. FTA-4089, which is described, for example, in U.S. Pat. No. 7,183,385; or antibodies as described in U.S. Pat. No. 5,548,065 (including, for instance, anti-CD135 antibodies, antigen-binding fragments thereof, and ligands produced and released by ATCC Accession Nos. CRL 10907, CRL 10935, CRL 10936, and CRL 11005).

Each of these targets is differentially expressed on hematopoietic stem and progenitor cells, and generally show reduced or no expression on mature differentiated hematopoietic stem cells. Thus, the compositions and methods of the present invention provide a novel way to target hematopoietic stem cells and deplete that population with minimal effect of other cells/tissues. According to certain aspects, the invention provides a method for depleting a subject's hematopoietic stem cells comprising administering to the subject an effective amount of a radiolabeled antibody, such as a radiolabeled anti-CD34, anti-CD117, or anti-CD135.

The effective amount of the radiolabeled antibody may be a maximum tolerated dose (MTD) or may be an amount sufficient to induce myeloconditioning or even myeloablation. Such treatment may be an effective precursor to transplantation with allogeneic or autologous stem cells and may provide improved treatment outcomes for a category of patients having poor outcomes with standard prior art therapies (i.e., radiation and/or chemotherapy).

According to certain aspects of the present invention, the methods comprise administering an effective amount of the radiolabeled antibody such as a radiolabeled anti-CD34, anti-CD117, or anti-CD135, for the treatment of a proliferative disease or malignant hematological disease.

This depletion method (also referred to herein as a conditioning method) is also useful in treatment methods for subjects afflicted with a cancerous disorder treatable via HSCT, e.g., bone marrow transplant. For example, the hematopoietic stem cells may be depleted or ablated and replaced after standard cancer treatments with high doses of chemotherapy or radiation that damage the bone marrow, or to replace diseased or damaged bone marrow, or to provide new stem cells that can kill cancer cells directly. As such, the present invention provides a method for treating a subject afflicted with a cancerous disorder comprising administering to the subject an amount of a radiolabeled antibody effective to deplete or ablate the subject's hematopoietic stem cells. According to certain aspects, the method may further comprise, after a suitable time period, performing a bone marrow transplant to treat the subject's disorder.

This depletion method is also useful for improving the outcome of a subsequent gene-edited cell-based therapy where the depletion of hematopoietic stem cells is desirable. According to certain preferred aspects of this method, the subject is afflicted with a non-cancerous disorder treatable via genetically edited cell therapy and is about to undergo such therapy to treat the disorder. As such, the present invention also provides a method for treating a subject afflicted with a non-cancerous disorder treatable via genetically edited cell therapy comprising administering to the subject an amount of a radiolabeled antibody effective to deplete the subject's hematopoietic stem cells. According to certain aspects, the method may further comprise, after a suitable time period, performing the therapy on the subject to treat the subject's disorder.

According to certain preferred aspects of the subject method, the radiolabeled antibody is radiolabeled with $^{131}$I or $^{225}$Ac. When the radiolabeled antibody is $^{131}$I-labeled, the effective amount can be, for example, from 10 mCi to 200 mCi, from 200 mCi to 400 mCi, or from 400 mCi to 1,200 mCi. When the radiolabeled antibody is $^{225}$Ac-labeled, the effective amount can be, for example, from 0.1 μCi/kg to 1.0 μCi/kg, from 1.0 μCi/kg to 3.0 μCi/kg, from 3.0 μCi/kg to 5.0 μCi/kg, or from 0.1 μCi/kg to 5.0 μCi/kg.

This invention provides, among other things, seven specific aspects of the subject method for treating a human subject afflicted with a cancerous disorder treatable via a bone marrow transplant. The first comprises (i) administering to the subject from 10 mCi to 200 mCi of the $^{131}$I-labeled antibody, and (ii) after 6, 7 or 8 days, performing the bone marrow transplant on the subject to treat the subject's cancer. The second comprises (i) administering to the subject from 200 mCi to 400 mCi of the $^{131}$I-labeled antibody, and (ii) after 8, 9, 10, 11 or 12 days, performing the bone marrow transplant on the subject to treat the subject's cancer. The third comprises (i) administering to the subject from 400 mCi to 1,200 mCi of the $^{131}$I-labeled antibody, and (ii) after 10, 11, 12, 13 or 14 days, performing the bone marrow transplant on the subject to treat the subject's cancer. The fourth comprises (i) administering to the subject from 0.1 μCi/kg to 5.0 μCi/kg of the $^{225}$Ac-labeled antibody, and (ii) after 6, 7 or 8 days, performing the bone marrow transplant on the subject to treat the subject's cancer. The fifth comprises (i) administering to the subject from 0.1 μCi/kg to 1.0 μCi/kg of the $^{225}$Ac-labeled antibody, and (ii) after 6, 7 or 8 days, performing the bone marrow transplant on the subject to treat the subject's cancer. The sixth comprises (i) administering to the subject from 1.0 μCi/kg to 3.0 μCi/kg of the $^{225}$Ac-labeled antibody, and (ii) after 6, 7 or 8 days, performing the bone marrow transplant on the subject to treat the subject's cancer. The seventh comprises (i) administering to the subject from 3.0 μCi/kg to 5.0 μCi/kg of the $^{225}$Ac-labeled antibody, and (ii) after 6, 7 or 8 days, performing the bone marrow transplant on the subject to treat the subject's cancer.

Exemplary cancers treated by these methods include at least lymphomas and/or leukemias. For example, the cancer may be lymphoblastic leukemia, multiple myeloma, myelodysplastic syndrome, non-Hodgkin's lymphoma, Hodgkin's lymphoma, chronic lymphocytic leukemia, or a combination thereof.

This invention provides, among other things, seven specific aspects of the subject method for treating a human subject afflicted with a non-cancerous disorder treatable via genetically edited allogeneic or autologous cell therapy. The first comprises (i) administering to the subject from 10 mCi to 200 mCi of the $^{131}$I-labeled antibody, and (ii) after 6, 7 or 8 days, performing the therapy on the subject to treat the subject's disorder. The second comprises (i) administering to the subject from 200 mCi to 400 mCi of the $^{131}$I-labeled antibody, and (ii) after 8, 9, 10, 11 or 12 days, performing the therapy on the subject to treat the subject's disorder. The third comprises (i) administering to the subject from 400 mCi to 1,200 mCi of the $^{131}$I-labeled antibody, and (ii) after 10, 11, 12, 13 or 14 days, performing the therapy on the subject to treat the subject's disorder. The fourth comprises (i) administering to the subject from 0.1 μCi/kg to 5.0 μCi/kg of the $^{225}$Ac-labeled antibody, and (ii) after 6, 7 or 8 days, performing the therapy on the subject to treat the subject's disorder. The fifth comprises (i) administering to the subject from 0.1 μCi/kg to 1.0 μCi/kg of the $^{225}$Ac-labeled antibody, and (ii) after 6, 7 or 8 days, performing the therapy on the subject to treat the subject's disorder. The sixth comprises (i) administering to the subject from 1.0 μCi/kg to 3.0 μCi/kg of the $^{225}$Ac-labeled antibody, and (ii) after 6, 7 or 8 days, performing the therapy on the subject to treat the subject's disorder. The seventh comprises (i) administering to the subject from 3.0 μCi/kg to 5.0 μCi/kg of the $^{225}$Ac-labeled antibody, and (ii) after 6, 7 or 8 days, performing the therapy on the subject to treat the subject's disorder.

This invention further provides an article of manufacture comprising (a) a radiolabeled antibody, and (b) a label instructing the user to administer to a subject an amount of the antibody effective to deplete the subject's hematopoietic stem cells. Preferably, the subject is human.

According to certain preferred aspects of the subject article, the radiolabeled antibody is radiolabeled CD34, or CD117, or CD135, such as with $^{131}$I or $^{225}$AC. When the radiolabeled antibody is $^{131}$I-labeled, the effective amount can be, for example, from 10 mCi to 200 mCi, from 200 mCi to 400 mCi, or from 400 mCi to 1,200 mCi. When the radiolabeled antibody is $^{225}$Ac-labeled, the effective amount can be, for example, from 0.1 μCi/kg to 5.0 μCi/kg.

This invention provides, among other things, seven specific aspects of the subject article. The first comprises (a) a $^{131}$I-labeled antibody, and (b) a label instructing the user to administer to a human subject from 10 mCi to 200 mCi of the $^{131}$I-labeled antibody. The second comprises (a) a $^{131}$I-labeled antibody, and (b) a label instructing the user to administer to a human subject from 200 mCi to 400 mCi of the $^{131}$I-labeled antibody. The third comprises (a) a $^{131}$I-labeled antibody, and (b) a label instructing the user to administer to a human subject from 400 mCi to 1,200 mCi of the $^{131}$I-labeled antibody. The fourth comprises (a) an $^{225}$Ac-labeled antibody, and (b) a label instructing the user to administer to a human subject from 0.1 μCi/kg to 5.0 μCi/kg of the $^{225}$Ac-labeled antibody. The fifth comprises (a) an $^{225}$Ac-labeled antibody, and (b) a label instructing the user to administer to a human subject from 0.1 μCi/kg to 1.0 μCi/kg of the $^{225}$Ac-labeled antibody. The sixth comprises (a) an $^{225}$Ac-labeled antibody, and (b) a label instructing the user to administer to a human subject from 1.0 μCi/kg to 3.0 μCi/kg of the $^{225}$Ac-labeled antibody. The seventh comprises (a) an $^{225}$Ac-labeled antibody, and (b) a label instructing the user to administer to a human subject from 3.0 μCi/kg to 5.0 μCi/kg of the $^{225}$Ac-labeled antibody.

Accordingly, the following aspects are disclosed in this application:

Aspect 1. A method for targeted depletion of a subject's hematopoietic stem cells, the method comprising: administering to the subject an effective amount of a radiolabeled antibody against CD34, CD117, CD135, or a combination thereof.

Aspect 2. The method according to aspect 1, wherein the radiolabeled antibody is labeled $^{131}$I, $^{125}$I, $^{123}$I, $^{90}$Y, $^{177}$Lu, $^{186}$Re, $^{188}$Re, $^{89}$Sr, $^{153}$Sm, $^{32}$P, $^{225}$Ac, $^{213}$Bi, $^{213}$Po, $^{211}$At, $^{212}$Bi, $^{213}$Bi, $^{223}$Ra, $^{227}$Th, $^{149}$Tb, $^{137}$Cs, $^{212}$Pb and $^{103}$Pd.

Aspect 3. The method according to aspect 2, wherein the radiolabeled antibody is $^{131}$I-labeled, and the effective amount of $^{131}$I-labeled antibody is from 10 mCi to 200 mCi, or from 200 mCi to 400 mCi, or from 400 mCi to 1,200 mCi.

Aspect 4. The method according to aspect 2, wherein the radiolabeled antibody is $^{225}$Ac-labeled, and the effective amount of $^{225}$Ac-labeled antibody is from 0.1 μCi/kg to 5.0 μCi/kg subject weight, or from 0.1 μCi/kg to 1.0 μCi/kg subject weight, or from 1.0 μCi/kg to 3.0 μCi/kg subject weight, or from 3.0 μCi/kg to 5.0 μCi/kg subject weight.

Aspect 5. The method according to any one of aspects 1 to 4, wherein the subject is afflicted with a non-cancerous disorder treatable via genetically edited cell therapy and is about to undergo such therapy to treat the disorder, and the effective amount of the radiolabeled antibody is administered as a single dose.

Aspect 6. The method according to aspect 5, wherein the disorder is selected from the group consisting of a hemoglobinopathy, a congenital immunodeficiency, and a viral infection.

Aspect 7. The method according to aspect 5, wherein the disorder is selected from the group consisting of sickle cell disease (SCD), severe combined immunodeficiency disease (SCID), and β-thalassemia.

Aspect 8. The method according to aspect 7, wherein the disorder is SCD and the therapy is genetically edited β-globin hematopoietic stem cell therapy.

Aspect 9. The method according to aspect 7, wherein the disorder is SCID and the therapy is genetically edited hematopoietic stem cell therapy, wherein the edited gene is selected from the group consisting of the common gamma chain (γc) gene, the adenosine deaminase (ADA) gene and the Janus kinase 3 (JAK3) gene.

Aspect 10. The method according to any one of aspects 1 to 9, wherein the hematopoietic stem cells are depleted by at least 50%, or at least 70%, or at least 90%.

Aspect 11. The method according to aspect 10, wherein mature differentiated hematopoietic stem cells are depleted by less than 20%, or less than 10%.

Aspect 12. The method according to any one of aspects 1 to 4, wherein the subject is afflicted with a cancerous disorder treatable by a bone marrow transplant.

Aspect 13. The method according to aspect 12, wherein the disorder is a leukemia or a lymphoma.

Aspect 14. The method according to aspect 12, wherein the disorder acute is lymphoblastic leukemia, multiple myeloma, myelodysplastic syndrome, non-Hodgkin's lymphoma, Hodgkin's lymphoma, chronic lymphocytic leukemia, or a combination thereof.

Aspect 15. A method for treating a subject afflicted with a cancerous disorder treatable via bone marrow transplant, the method comprising: (i) administering to the subject an amount of a radiolabeled antibody effective to deplete or ablate the subject's hematopoietic stem cells, and (ii) after a suitable time period, performing the bone marrow transplant on the subject to treat the subject's disorder, wherein the antibody comprises anti-CD34, anti-CD117, anti-CD135, or a combination thereof.

Aspect 16. The method according to aspect 15, wherein the disorder is a leukemia or a lymphoma.

Aspect 17. The method according to any one of aspects 15 to 16, wherein the disorder acute is lymphoblastic leukemia, multiple myeloma, myelodysplastic syndrome, non-Hodgkin's lymphoma, Hodgkin's lymphoma, chronic lymphocytic leukemia, or a combination thereof.

Aspect 18. The method according to any one of aspects 15 to 17, wherein the hematopoietic stem cells are depleted by or at least 70%, or at least 90%; and the mature differentiated hematopoietic stem cells are depleted by less than 20%, or less than 10%.

Aspect 19. The method according to any one of aspects 15 to 18, wherein the radiolabeled antibody is labeled with $^{131}$I, $^{125}I$, $^{123}I$, $^{90}Y$, $^{177}Lu$, $^{186}Re$, $^{188}Re$, $^{89}Sr$, $^{153}Sm$, $^{32}P$, $^{225}Ac$, $^{213}Bi$, $^{213}Po$, $^{211}At$, $^{212}Bi$, $^{213}Bi$, $^{223}Ra$, $^{227}Th$, $^{149}Tb$, $^{137}Cs$, $^{212}Pb$ or $^{103}Pd$.

Aspect 20. The method according to any one of aspects 15 to 19, wherein the radiolabeled antibody is $^{131}I$-labeled, and the effective amount of $^{131}I$-labeled antibody is from 10 mCi to 200 mCi administered 6, 7, or 8 days before the bone marrow transplant.

Aspect 21. The method according to any one of aspects 15 to 19, wherein the radiolabeled antibody is $^{131}I$-labeled, and the effective amount of $^{131}I$-labeled antibody is from 200 mCi to 400 mCi administered 8, 9, 10, 11, or 12 days before the bone marrow transplant.

Aspect 22. The method according to any one of aspects 15 to 19, wherein the radiolabeled antibody is $^{131}I$-labeled, and the effective amount of $^{131}I$-labeled antibody is from 400 mCi to 1,200 mCi administered 10, 11, 12, 13, or 14 days before the bone marrow transplant.

Aspect 23. The method according to any one of aspects 15 to 19, wherein the radiolabeled antibody is $^{225}Ac$-labeled, and the effective amount of $^{225}Ac$-labeled antibody is from 0.1 μCi/kg to 5.0 μCi/kg subject weight administered 6, 7, 8, 9, 10, 11, or 12 days before the bone marrow transplant.

Aspect 24. A method for treating a subject afflicted with a non-cancerous disorder treatable via genetically edited cell therapy comprising (i) administering to the subject an amount of a radiolabeled antibody effective to deplete the subject's hematopoietic stem cells, and (ii) after a suitable time period, performing the therapy on the subject to treat the subject's disorder, wherein the antibody comprises anti-CD34, anti-CD117, anti-CD135, or a combination thereof.

Aspect 25. The method according to aspect 24, wherein the subject is afflicted with a non-cancerous disorder treatable via genetically edited cell therapy and is about to undergo such therapy to treat the disorder, and the effective amount of the radiolabeled antibody is administered as a single dose.

Aspect 26. The method according to aspect 24 or 25, wherein the disorder is selected from the group consisting of a hemoglobinopathy, a congenital immunodeficiency, and a viral infection.

Aspect 27. The method according to any one of aspects 24 to 26, wherein the disorder is selected from the group consisting of sickle cell disease (SCD), severe combined immunodeficiency disease (SCID), and β-thalassemia.

Aspect 28. The method according to aspect 27, wherein the disorder is SCD and the therapy is genetically edited β-globin hematopoietic stem cell therapy.

Aspect 29. The method according to aspect 27, wherein the disorder is SCID and the therapy is genetically edited hematopoietic stem cell therapy, wherein the edited gene is selected from the group consisting of the common gamma chain (γc) gene, the adenosine deaminase (ADA) gene and the Janus kinase 3 (JAK3) gene.

Aspect 30. The method according to aspect 28 or 29, wherein the stem cell therapy is allogeneic stem cell therapy, or wherein the stem cell therapy is autologous stem cell therapy.

Aspect 31. The method according to any one of aspects 24 to 30, wherein the radiolabeled antibody is labeled with $^{131}I$, $^{125}I$, $^{123}I$, $^{90}Y$, $^{177}Lu$, $^{186}Re$, $^{188}Re$, $^{89}Sr$, $^{153}Sm$, $^{32}P$, $^{225}Ac$, $^{213}Bi$, $^{213}Po$, $^{211}At$, $^{212}Bi$, $^{213}Bi$, $^{223}Ra$, $^{227}Th$, $^{149}Tb$, $^{137}Cs$, $^{212}Pb$ or $^{103}Pd$.

Aspect 32. The method according to any one of aspects 24 to 31, wherein the radiolabeled antibody is $^{131}I$-labeled, and the effective amount of $^{131}I$-labeled antibody is from 10 mCi to 200 mCi administered 6, 7, or 8 days before performing the therapy on the subject to treat the subject's disorder.

Aspect 33. The method according to any one of aspects 24 to 31, wherein the radiolabeled antibody is $^{131}I$-labeled, and the effective amount of $^{131}I$-labeled antibody is from 200 mCi to 400 mCi administered 8, 9, 10, 11, or 12 days before performing the therapy on the subject to treat the subject's disorder.

Aspect 34. The method according to any one of aspects 24 to 31, wherein the radiolabeled antibody is $^{131}I$-labeled, and the effective amount of $^{131}I$-labeled antibody is from 400 mCi to 1,200 mCi administered 10, 11, 12, 13, or 14 days before performing the therapy on the subject to treat the subject's disorder.

Aspect 35. The method according to any one of aspects 24 to 31, wherein the radiolabeled antibody is $^{225}Ac$-labeled, and the effective amount of $^{225}Ac$-labeled antibody is from 0.1 μCi/kg to 5.0 μCi/kg subject weight administered 6, 7, 8, 9, 10, 11, or 12 days before performing the therapy on the subject to treat the subject's disorder.

Aspect 36. An article of manufacture comprising (a) a radiolabeled antibody, and (b) a label instructing the user to administer to a subject an amount of the antibody effective to deplete the subject's hematopoietic stem cells, wherein the antibody comprises anti-CD34, anti-CD117, anti-CD135, or a combination thereof.

Aspect 37. The article according to aspect 36, wherein the radiolabeled antibody is $^{131}I$-labeled, and the effective amount of $^{131}I$-labeled antibody is from 10 mCi to 200 mCi, or from 200 mCi to 400 mCi, or from 400 mCi to 1,200 mCi.

Aspect 38. The article according to aspect 36, wherein the radiolabeled antibody is $^{225}Ac$-labeled, and the effective amount of $^{225}Ac$-labeled antibody is from 0.1 μCi/kg to 5.0 μCi/kg, or from 0.1 μCi/kg to 1.0 μCi/kg subject weight, or from 1.0 μCi/kg to 3.0 μCi/kg subject weight, or from 3.0 μCi/kg to 5.0 μCi/kg subject weight.

This invention will be better understood by reference to the examples which follow, but those skilled in the art will readily appreciate that the specific examples detailed are only illustrative of the invention as described more fully in the claims which follow thereafter.

Examples

Example 1—Radio-Iodination of Antibodies

Commercially available anti-CDXX antibodies and antibodies generated by methods known in the art from CDXX-positive cell lines for each of CD34, CD117, and CD135, available from the ATCC as detailed herein may be labelled with Iodine-131 ($^{131}I$).

A specific example for labeling an anti-CDXX antibody with $^{131}I$ includes: One (1) mg of anti-CDXX immunoglobulin as described herein may be labeled with 20 to 30 mCi of $^{131}I$—Na (30 mCi) in the presence of chloramine-T (23 micrograms) in PBS buffer (pH 7.2). The reaction may then be quenched with the addition of aqueous sodium thiosulfate (69 micrograms) and diluted with cold NaI (1 mg). Immediately following, a concentrated ascorbic acid solution made in 50 mM PBS (pH 7) may be added to achieve 2.5% (w/v) ascorbic acid strength in the quenched reaction mixture. Labeling reactions up to 3,000 mCi per batch may be successfully performed using this method.

The labeled product may be purified by gel filtration on a sterile, pre-packed commercially available Sephadex G25 column (GE HiPrep 26/10 column, bed volume 53 mL) using PBS (50 mM, pH 7) mobile phase supplemented with 2.5% (w/v) ascorbic acid to stabilize the radiolabeled product. Up to 1,000 mCi reaction volume may be purified on a single column, with product collected in a 5 mL to 35 mL elution volume.

The radio-iodinated reaction batches of <200 mCi could be purified in a similar fashion on a smaller desalting column (GE PD10 column, bed volume 8.6 mL).

Example 2—Actinium Labeling of Antibodies

Commercially available anti-CDXX antibodies and antibodies generated by methods known in the art from CDXX-positive cell lines for each of CD34, CD117, and CD135, available from the ATCC as detailed herein may be labelled with Actinium-225 ($^{225}$Ac). Isotype control human IgG's, may be purchased from Creative Diagnostics (New York, USA). Actinium-225 ($^{225}$Ac) in dry nitrate form may be obtained from Oak Ridge National Laboratory, USA. The bifunctional chelating agent p-SCN-Bn-DOTA (referred to as DOTA in these examples) may be purchased from Macrocyclics (Texas, USA).

DOTA may be conjugated to the anti-CDXX at excess, e.g., 5M, for 1.5 h at 37° C. in ammonium acetate buffer. The anti-CDXX-DOTA conjugate may then be labeled with $^{225}$Ac in 0.01M HCL (pH 6.5) at luCi/ug anti-CDXX for 60 minutes at 37° C. or room temperature, providing a specific activity of about 100 nCi-500 nCi to 0.3 μg $^{225}$Ac-anti-CDXX. The $^{225}$Ac-anti-CDXX may be diluted with unlabeled anti-CDXX to adjust for total antibody dose and radiation (radiolabel) dose. The samples may be purified on disposable spin columns to 99±1% purity.

A specific labeling example for conjugation of anti-CDXX with the chelating agent DOTA may include: the antibody (2 mg) may be equilibrated with conjugation buffer (Na carbonate buffer with 1 mM EDTA, pH=8.5-9.0) by four ultrafiltration spins on a Centricon filter or Vivaspin ultrafiltration tube with a MW cutoff of appropriate size (e.g., 50,000). A volume of 1.5 ml conjugation buffer per spin may be used. For each spin, the antibody may be spun for 5-20 minutes, at 53,000 RPM and at 4° C. to a residual retentate volume of 100-200 μl. The antibody may be incubated at 4° C. for 30 minutes following the 2nd and 3rd spins to allow for equilibration. For DOTA conjugation, a solution of S-2-(4-Isothiocyanatobenzyl)-1,4,7,10 tetra-azacyclododecanetetraacetic acid (p-SCN-Bz-DOTA; MW=687) at 3 mg/ml in 0.15M $NH_4OAc$ may be prepared by dissolution and vortexing. DOTA-Bz-pSCN and anti-CDXX antibody (at >5 mg/ml) may be mixed together at a 7.5 molar ratio (DOTA:antibody) in an Eppendorf tube and incubated for 15 hours at room temperature. For purification of the DOTA-antibody conjugate, unreacted DOTA-Bz-pSCN may be removed by seven rounds of ultrafiltration with 1.5 ml of 0.15M NH4OAc buffer, pH=6.5 to a volume of approximately 100 μl. After the final wash, 0.15 M $NH_4OAc$ buffer was added to bring the material to a final concentration of approximately 1 mg/ml. Using this method, the number of DOTA molecules conjugated to the anti-CDXX antibody is generally 1.2-1.5 DOTA to antibody.

A specific labeling example for radiolabeling of the DOTA-antibody conjugates with $^{225}$Ac may include: mixing 15 μL 0.15M $NH_4OAc$ buffer, pH=6.5 with 2 μL (10 μg) DOTA-CDXX (5 mg/ml) in an Eppendorf reaction tube. Four (4) μL of $^{225}$Ac (10 μCi) in 0.05 M HCl may be added, mixed, and the reaction mixture incubated at 37° C. for 90 minutes with shaking at 100 rpm. At the end of the incubation period, 3 μL of 1 mM DTPA solution may be added to the reaction mixture and incubated at room temperature for 20 minutes to bind un-complexed $^{225}$Ac. Instant thin layer chromatography (ITLC) may be performed with a 10 cm silica gel strip and a 10 mM EDTA/normal saline mobile phase to determine the radiochemical purity of the $^{225}$Ac-anti-CDXX, separating the $^{225}$Ac-labeled antibody from $^{225}$Ac-DTPA and counting sections in a gamma counter equipped with a multichannel analyzer. The radiolabeling efficiency over several runs has been determined to be greater than 80% for standard antibodies.

Example 3—Patient Specific Therapeutic

The radiolabeled anti-CDXX ("drug product") may be supplied for patient administration as a sterile formulation contained in a container closure system consisting of a depyrogenated Type 1 50 mL glass vial, sterilized grey chlorobutyl rubber stopper, and open top style aluminum seal. Each dose vial may contain a drug product fill volume of 45 mL in a 50 mL vial. Similarly, the drug product may be provided as a single use dose for complete infusion during intravenous administration and may contain a patient-specific radioactivity. For $^{131}$I-anti-CDXX, the patient-specific dose may include from 1 mCi to 1200 mCi, as described herein, of $^{131}$I and 1-60 mg of protein (total anti-CDXX). For $^{225}$Ac-anti-CDXX, the patient-specific dose may include from 00.1 μCi/kg to 5.0 μCi/kg patient weight, as described herein, of $^{225}$Ac and 1-60 mg of protein (total anti-CDXX). The anti-CDXX antibody dose is determined according to the ideal body weight at a level of 0.1 mg/kg to 1.0 mg/kg, such as 0.5 mg/kg. according to certain aspects, the drug product may be co-administered in-line with 0.9% Sodium Chloride Injection USP (normal saline solution) to the patient at a ratio of 1:9 of drug product to saline solution. The total drug product and saline infusion volume of approximately 430-450 mL is administered over varied durations, since the infusion rate depends on the amount of anti-CDXX antibody in the 45 mL drug product fill volume.

Example 4—SCD

This example describes HSC ablation (i.e., 100% depletion) preceding transplant with gene-edited HSCs in patients with SCD.

SCD is the most common hemoglobinopathy worldwide. The incidence of SCD among African Americans is approximately 1 in 500. It is estimated that 100,000 individuals are afflicted in the United States.

SCD is caused by a single nucleotide mutation in the β-globin gene that produces sickle hemoglobin. SCD patients may exhibit anemia, vaso-occlusive crises (VOCs), hemolysis, chronic organ dysfunction, and early mortality. The mortality rate among children with SCD is 0.5 per 100,000. However, the mortality rate in adults is more than 2.5 per 100,000, and median life expectancy is less than 50 years of age for both men and women with SCD.

Currently, the only curative treatment for SCD is a hematopoietic stem cell transplant (HSCT). Unfortunately, HSCTs for SCD are not without problems. According to the Center for International Blood and Marrow Transplant Research, only 1,089 patients with SCD underwent HSCTs from 1991 to April 2017. Risks associated with HSCTs include complications (such as graft-versus-host disease) arising from the use of allogeneic donor stem cells.

With the advent of gene editing technologies, there is now an opportunity to cure SCD patients using autologous stem cells in which the mutation in the β-globin gene responsible for SCD has been corrected. ZFN, TALEN, CRISPR/cas9 and other nuclease-mediated editing approaches could be used to repair, or remove and replace, stem cells from an SCD patient. For example, Sun and Zhao (Biotech. and Bioeng., 2014, 111(5)) demonstrated the successful repair of the human β-globin gene mutation in patient pleuripotent HSCs using TALENs. In addition, Dever, et al., (Nature, 2016, 539:384-389) demonstrated efficient repair of the Glu6Val mutation responsible for SCD in patient HSCs using CRISPR/cas9. Clinical trials using this approach for SCD are now starting.

Unfortunately, standard myeloablative conditioning regimens (i.e., 100% HSC-depleting regimens) using high dose chemotherapy or total body irradiation are currently used for transplants, including for autologous gene-edited cell transplants. There is a need for a safer and more effective conditioning method for these patients. Radiolabeled antibodies would be more sparing of a patient's normal tissues. Notably, older patients with SCD may already have organ damage as a result of their disease, and exposure to non-specific radiation or chemotherapy as a myeloablative conditioning regimen could make performing a stem cell transplant even riskier. A radiolabeled anti-CDXX approach presents a better option for these patients.

Further, due to the hereditary nature of the disease, correcting the disease through transplantation of gene-edited HSCs is preferred as early in life as possible, as complications of the disease may be irreversible and have a negative impact on long-term survival for the patient. As such, treating infants or young children afflicted with SCD using gene-edited HSCs is envisioned. To this end, radiolabeled antibodies such as anti-CD34, anti-CD117, or anti-CD135, preferably labeled with an alpha-emitting radionuclide such as $^{225}$Ac, would be ideal. The use of an alpha-emitting radionuclide such as $^{225}$Ac, with its very short, high energy radiation path length, would focus the radiation on CD34-, CD117-, or CD135-positive cells and allow for effective ablation without the need to isolate the treated patients (as would be required for conditioning with an ablative dose of an $^{131}$I-labeled antibody).

Example 5—SCID

This example describes HSC ablation preceding transplantation with gene-edited HSCs in patients with SCID.

SCID is a germline genetic disorder in which afflicted patients present with severe T cell defects, with or without accompanying B cell defects. SCID involves a defective adaptive immune response that prevents patients from mounting an effective antibody response to pathogens. SCID is the most severe form of primary immunodeficiencies, and there are at least nine different known genes where mutations lead to SCID. Because SCID patients are incapable of mounting an adaptive immune response, they are susceptible to infection, and early mortality is high. SCID is also known as the "bubble boy" disease because patients must be kept in a sterile environment to avoid life-threatening infections.

The most frequent genetic defect in SCID is in the common gamma chain (γc), which is a protein that is shared by the receptors for interleukins IL-2, IL-4, IL-7, IL-9, IL-15 and IL-21. Other mutated genes that can lead to SCID are ADA and JAK3. As with SCD, only treatment with a stem cell transplant is potentially curative for SCID. However, delayed immune recovery and GVHD are significant risks for these patients. Also, as with SCD patients, SCID patients are young and therefore need effective and safe methods for treatment, including a better conditioning regimen prior to transplant.

Gene editing technology may precisely repair the defect in a SCID patient's own HSCs. Once returned to the body, these engineered HSCs can produce normal lymphocytes and establish a working adaptive immune response to protect against infection. Recently, Chang et al (Cell Reports, 2015, 12:1668-1677) reported effectively restoring normal lymphocyte development via CRISPR/cas9-mediated repair of a mutation in the JAK3 gene in mice. Further Alzubi, et al., (Nature, Scientific Reports, 2017, 7:12475) recently demonstrated using TALEN technology to precisely repair in mice a genetic defect in the IL2RG (common gamma chain), the gene responsible for X-SCID.

It is important that safer and more effective methods for conditioning human SCID patients are developed. Alpha-emitter radioimmunotherapy, such as with $^{225}$Ac-labeled anti-CD34 or anti-CD117, or anti-CD135, is needed to safely condition these predominantly young patients.

Example 6—Treatment Synopsis

Table I summarizes selected treatment regimens using gene-edited stem cell administration preceded by HSC depletion via administration of a radiolabeled antibody (i.e., conditioning agent).

TABLE 1

| Disease | Therapy | Conditioning Agent | Dose |
|---|---|---|---|
| SCD | Gene-edited HSCs or Pleuripotent Stem Cells (PSCs) [genes repaired include b-globin (HBB)] | $^{131}$I-anti-CD34<br>$^{131}$I-anti-CD117<br>$^{131}$I-anti-CD135<br>$^{225}$Ac-anti-CD34<br>$^{225}$Ac-anti-CD117<br>$^{225}$Ac-anti-CD135 | 200-1,200 mCi<br>[e.g., 200-400 mCi, or 400-1,200 mCi]<br>0.1-5 μCi/kg<br>[e.g., 0.1-1 μCi/kg, 1-3 μCi/kg, or 3-5 μCi/kg] |
| SCID | Gene-edited HSCs or PSCs [genes repaired include JAK3, Janus Family Kinase, ADA, adenosine deaminase, IL2RG, common gamma chain gene] | $^{131}$I-anti-CD34<br>$^{131}$I-anti-CD117<br>$^{131}$I-anti-CD135<br>$^{225}$Ac-anti-CD34<br>$^{225}$Ac-anti-CD117<br>$^{225}$Ac-anti-CD135 | 200-1,200 mCi<br>[e.g., 200-400 mCi, or 400-1,200 mCi]<br>0.1-5 μCi/kg<br>[e.g., 0.1-1 μCi/kg, 1-3 μCi/kg, or 3-5 μCi/kg] |
| β-Thalassemia | Gene-edited HSCs or PSCs [genes repaired include b-globin (HBB), BCL11A] | $^{131}$I-anti-CD34<br>$^{131}$I-anti-CD117<br>$^{131}$I-anti-CD135<br>$^{225}$Ac-anti-CD34<br>$^{225}$Ac-anti-CD117<br>$^{225}$Ac-anti-CD135 | 200-1,200 mCi<br>[e.g., 200-400 mCi, or 400-1,200 mCi]<br>0.1-5 μCi/kg<br>[e.g., 0.1-1 μCi/kg, 1-3 μCi/kg, or 3-5 μCi/kg] |

TABLE 1-continued

| Disease | Therapy | Conditioning Agent | Dose |
|---|---|---|---|
| Wiskott-Aldrich Syndrome | Gene-edited HSCs or PSCs [genes repaired include WAS] | $^{131}$I-anti-CD34<br>$^{131}$I-anti-CD117<br>$^{131}$I-anti-CD135<br>$^{225}$Ac-anti-CD34<br>$^{225}$Ac-anti-CD117<br>$^{225}$Ac-anti-CD135 | 200-1,200 mCi<br>[e.g., 200-400 mCi, or 400-1,200 mCi]<br>0.1-5 μCi/kg<br>[e.g., 0.1-1 μCi/kg, 1-3 μCi/kg, or 3-5 μCi/kg] |
| AIDS | Gene-edited HSCs or PSCs [genes repaired include CCR5 and CXCR4] | $^{131}$I-anti-CD34<br>$^{131}$I-anti-CD117<br>$^{131}$I-anti-CD135<br>$^{225}$Ac-anti-CD34<br>$^{225}$Ac-anti-CD117<br>$^{225}$Ac-anti-CD135 | 200-1,200 mCi<br>[e.g., 200-400 mCi, or 400-1,200 mCi]<br>0.1-5 μCi/kg<br>[e.g., 0.1-1 μCi/kg, 1-3 μCi/kg, or 3-5 μCi/kg] |

What is claimed is:

1. A method for targeted depletion of a subject's hematopoietic stem cells, the method comprising:
   - administering to the subject an effective amount of a conjugation of a radiolabeled antibody against CD135 and a bifunctional chelating agent,
   - wherein the bifunctional chelating agent is p-SCN-Bn-DOTA, and
   - wherein the radiolabeled antibody comprises a radiolabel selected from $^{90}$Y, $^{177}$Lu, $^{186}$Re, $^{188}$Re, $^{153}$Sm, $^{225}$Ac, $^{212}$Bi, $^{213}$Bi, $^{227}$Th, $^{149}$Tb, and $^{212}$Pb.

2. The method of claim 1, wherein the radiolabel is $^{225}$Ac, and the effective amount of the radiolabeled antibody comprises a radiation does from 0.1 μCi/kg to 5.0 μCi/kg subject weight, or from 0.1 μCi/kg to 1.0 μCi/kg subject weight, or from 1.0 μCi/kg to 3.0 μCi/kg subject weight, or from 3.0 μCi/kg to 5.0 μCi/kg subject weight.

3. A method for targeted depletion of a subject's hematopoietic stem cells, the method comprising:
   - administering to the subject an effective amount of a conjugation of a radiolabeled antibody against CD135 and a bifunctional chelating agent,
   - wherein the bifunctional chelating agent is p-SCN-Bn-DOTA,
   - wherein the radiolabeled antibody comprises a radiolabel selected from $^{90}$Y, $^{177}$Lu, $^{186}$Re, $^{188}$Re, $^{153}$Sm, $^{225}$Ac, $^{212}$Bi, $^{213}$Bi, $^{227}$Th, $^{149}$Tb, and $^{212}$Pb,
   - wherein the subject is afflicted with a non-cancerous disorder treatable via genetically edited cell therapy and is about to undergo such therapy to treat the non-cancerous disorder, and the effective amount of the radiolabeled antibody is administered as a single dose, and
   - wherein the non-cancerous disorder is selected from the group consisting of sickle cell disease (SCD), severe combined immunodeficiency disease (SCID), and β-thalassemia.

4. The method of claim 3, wherein the non-cancerous disorder is SCD and the therapy is genetically edited β-globin hematopoietic stem cell therapy.

5. The method of claim 3, wherein the disorder is SCID and the therapy is genetically edited hematopoietic stem cell therapy, wherein the edited gene is selected from the group consisting of the common gamma chain (γc) gene, the adenosine deaminase (ADA) gene and the Janus kinase 3 (JAK3) gene.

6. The method of claim 1, wherein the hematopoietic stem cells are depleted by at least 50% and wherein mature differentiated hematopoietic stem cells are depleted by less than 20%.

7. The method of claim 1, wherein the subject is afflicted with a cancerous disorder treatable by a bone marrow transplant, wherein the cancerous disorder is a leukemia or a lymphoma.

8. The method of claim 7, wherein the cancerous disorder acute is lymphoblastic leukemia, multiple myeloma, myelodysplastic syndrome, non-Hodgkin's lymphoma, Hodgkin's lymphoma, chronic lymphocytic leukemia, or a combination thereof.

9. A method for treating a subject afflicted with a cancerous disorder treatable via bone marrow transplant, the method comprising:
   - (i) administering to the subject an amount of a radiolabeled antibody effective to deplete or ablate the subject's hematopoietic stem cells; and
   - (ii) after a suitable time period, performing the bone marrow transplant on the subject to treat the subject's disorder,
   - wherein the cancerous disorder is a leukemia or a lymphoma and the antibody comprises a conjugate of an anti-CD135 monoclonal antibody and a bifunctional chelating agent, wherein the bifunctional chelating agent is p-SCN-Bn-DOTA,
   - wherein the radiolabeled antibody is labeled with $^{90}$Y, $^{177}$Lu, $^{186}$Re, $^{188}$Re, $^{153}$Sm, $^{225}$Ac, $^{212}$Bi, $^{213}$Bi, $^{227}$Th, $^{149}$Tb, or $^{212}$Pb.

10. The method of claim 9, wherein the cancerous disorder acute is lymphoblastic leukemia, multiple myeloma, myelodysplastic syndrome, non-Hodgkin's lymphoma, Hodgkin's lymphoma, chronic lymphocytic leukemia, or a combination thereof.

11. The method of claim 9, wherein the hematopoietic stem cells are depleted by or at least 70%, and mature differentiated hematopoietic stem cells are depleted by less than 20%.

12. The method of claim 9, wherein the radiolabeled antibody comprises an $^{225}$Ac-radiolabel, and the effective amount of the $^{225}$Ac-radiolabel is from 0.1 μCi/kg to 5.0 μCi/kg subject weight administered 6, 7, 8, 9, 10, 11, or 12 days before the bone marrow transplant.

13. The method of claim 1, wherein the subject is afflicted with a CD135 (FLT-3) mutation in acute myeloid leukemia.

14. A method for targeted depletion of a subject's hematopoietic stem cells, the method comprising:
   - administering to the subject an effective amount of a radiolabeled antibody comprising a conjugate of an anti-CD135 monoclonal antibody and a bifunctional chelating agent,
   - wherein the bifunctional chelating agent is p-SCN-Bn-DOTA, wherein the radiolabeled antibody comprises a radiolabel selected from $^{90}$Y, $^{177}$Lu, $^{186}$Re, $^{188}$Re, $^{153}$Sm, $^{225}$Ac, $^{212}$Bi, $^{213}$Bi, $^{227}$Th, $^{149}$Tb, and $^{212}$Pb and wherein the subject is afflicted with a CD135 (FLT-3) mutation in acute myeloid leukemia.

15. The method of claim 1, wherein the radiolabeled antibody comprises a radiolabel selected from $^{90}$Y, $^{177}$Lu, or $^{225}$Ac.

16. The method of claim 3, wherein the radiolabeled antibody comprises a radiolabel selected from $^{90}$Y, $^{177}$Lu, or $^{225}$Ac.

17. The method of claim 9, wherein the radiolabeled antibody comprises a radiolabel selected from $^{90}$Y, $^{177}$Lu, or $^{225}$Ac.

18. The method of claim 14, wherein the radiolabeled antibody comprises a radiolabel selected from $^{90}$Y, $^{177}$Lu, or $^{225}$Ac.

* * * * *